US012781173B2

(12) United States Patent
Hanisch et al.

(10) Patent No.: US 12,781,173 B2
(45) Date of Patent: Nov. 3, 2026

(54) INLAY FOR A FLASK AND METHOD FOR INSERTING AN INLAY INTO A FLASK

(71) Applicant: Hochschule für angewandte Wissenschaften München, Munich (DE)

(72) Inventors: Patrick Hanisch, Hebertshausen (DE); Robert Huber, Oberaudorf (DE)

(73) Assignee: HOCHSCHULE FÜR ANGEWANDTE WISSENSCHAFTEN MÜNCHEN, Munich (DE)

( * ) Notice: Subject to any disclaimer, the term of this patent is extended or adjusted under 35 U.S.C. 154(b) by 0 days.

(21) Appl. No.: 18/759,116

(22) Filed: Jun. 28, 2024

(65) Prior Publication Data

US 2025/0011702 A1 Jan. 9, 2025

(30) Foreign Application Priority Data

Jul. 4, 2023 (EP) .................................... 23183188

(51) Int. Cl.
*C12M 1/00* (2006.01)
*C12M 1/24* (2006.01)

(52) U.S. Cl.
CPC ............ *C12M 27/20* (2013.01); *C12M 23/08* (2013.01); *C12M 23/26* (2013.01)

(58) Field of Classification Search
CPC ...... C12M 23/08; C12M 23/26; C12M 27/20; B01L 3/505
See application file for complete search history.

(56) References Cited

U.S. PATENT DOCUMENTS 2,362,354 A 11/1944 Clovis
4,550,848 A 11/1985 Sucato
(Continued)

FOREIGN PATENT DOCUMENTS

CN 101932693 12/2010
CN 205295334 6/2016
(Continued)

OTHER PUBLICATIONS

Bähr et al., "Dialysis shake flask for effective screening in fedbatch mode", Biochemical Engineering Journal, vol. 69, 2012, Germany, pp. 182-195.
(Continued)

*Primary Examiner* — Charles Capozzi
*Assistant Examiner* — Tingchen Shi
(74) *Attorney, Agent, or Firm* — Secant IP, PLLC

(57) ABSTRACT

An inlay for a flask comprising a bottom portion, a side portion, an intermediate portion, and a baffle element. The bottom portion comprises a downward-facing or downward-and-outwardfacing first surface for abutting a bottom inner surface of the flask. The side portion comprises an outer surface for abutting a side inner surface of the flask, wherein the outer surface faces outwards with respect to a vertical reference line intersecting the inlay. The intermediate portion mechanically connects the bottom portion and the side portion. The baffle element extends away from the bottom portion, from the side portion, and/or from the intermediate portion for extending into an inner volume of the flask. An inner angle between the first surface and the outer surface is at least 50°, wherein the inner angle refers to an angle on the side of the vertical reference line in a vertical cross section through the inlay. The inlay comprises a first flexible material adapted to allow for bending said side portion inwards. The inlay is adapted to allow for folding the inlay with
(Continued)

respect to a horizontal crease line to insert the inlay into the flask. The inlay comprises, along a vertical plane comprising the horizontal crease line, a second flexible material to allow for said folding.

13 Claims, 13 Drawing Sheets

(56) References Cited

U.S. PATENT DOCUMENTS

| | | | | |
|---|---|---|---|---|
| 4,665,035 | A | 5/1987 | Tunac | |
| 6,588,622 | B1 | 7/2003 | Leishman et al. | |
| 2010/0248995 | A1 | 9/2010 | Kensey et al. | |
| 2018/0000271 | A1 * | 1/2018 | Macneil | A47G 27/0206 |
| 2018/0201891 | A1 * | 7/2018 | Ubukata | C12M 23/22 |
| 2021/0380915 | A1 * | 12/2021 | Rao | C12M 23/08 |
| 2023/0193344 | A1 * | 6/2023 | Zarzycki | C12M 41/44 |

FOREIGN PATENT DOCUMENTS

| | | |
|---|---|---|
| CN | 205295335 | 6/2016 |
| CN | 106085853 | 11/2016 |
| CN | 211255913 | 8/2020 |
| GB | 1243750 | 8/1971 |
| JP | 2853950 | 2/1999 |
| WO | 87/07293 | 12/1987 |
| WO | 2019/219465 | 11/2019 |
| WO | 2021/228613 | 11/2021 |

OTHER PUBLICATIONS

Gamboa-Suasnavart et al., "The O-mannosylation and production of recombinant APA (45/47 KDa) protein from Mycobacterium tuberculosis in *Streptomyces* lividans is affected by culture conditions in shake flasks", Microbial Cell Factories, vol. 10, No. 110, 2011, Mexico, pp. 1-11.

Hansen et al., "Implementation of Perforated Concentric Ring Walls Considerably Improves Gas-Liquid Mass Transfer of Shaken Bioreactors", Frontiers in Bioengineering and Biotechnology, vol. 10, 2022, Germany, pp. 1-13.

Murray et al., "Wirelessly powered submerged-light illuminated photobioreactors for efficient microalgae cultivation", Algal Research, vol. 25, 2017, Switzerland, pp. 244-251.

Nedbal et al., "Bottom-illuminated orbital shaker for microalgae cultivation", HardwareX, vol. 8, 2020, Germany, pp. 1-12.

Palacios-Morales et al., "The flow inside shaking flasks and its implication for mycelial cultures", Chemical Engineering Science, vol. 152, 2016, Mexico, pp. 163-171.

ReynosoCereceda et al., "Shaken flasks by resonant acoustic mixing versus orbital mixing: Mass transfer coefficient kLa characterization and *Escherichia coli* cultures comparison", Biochemical Engineering Journal, vol. 105, 2016, Mexico, pp. 379-390.

Running et al., "Oxygen Transfer Rates in Shaken Culture Vessels From Fernbach Flasks to Microtiter Plates", Biotechnology and Bioengineering, vol. 113, No. 8, 2016, Indiana, pp. 1729-1735.

Tissot et al., "Helical-Track Bioreactors for Bacterial, Mammalian and Insect Cell Cultures", Processes, vol. 1, 2013, Switzerland, pp. 3-11.

Wang et al., "Bayesian Optimization for Hydrodynamic Characterization of a Cylindrical Orbitally Shaken Bioreactor with a Bump at the Bottom", Journal of Chemical Engineering of Japan, vol. 54, No. 9, 2021, Japan, pp. 493-499.

Extended European Search Report from related EPO Appln. No. 23183188.4, dated Feb. 26, 2024.

* cited by examiner

INLAY FOR A FLASK AND METHOD FOR INSERTING AN INLAY INTO A FLASK

CROSS-REFERENCE TO RELATED APPLICATIONS

The instant application claims priority to European Patent Application EP23183188.4, filed Jul. 4, 2023, which is incorporated herein in its entirety by reference.

FIELD

The disclosure relates to an inlay for a flask, such as a shake flask for cultivating microorganisms, in particular to improve the oxygen transfer into a liquid in the flask, and/or with improved sensoric access to the liquid, for example, to determine the oxygen content of the liquid.

BACKGROUND

Microorganisms are cultivated in different apparatus, adapted to the specific needs of the respective microorganism. Aerobic microorganisms require oxygen. In cultivating apparatus typically used at the lab scale, the oxygen is provided into a solution with the microorganism, by keeping the solution in a flask, and shaking the flask with a permeable closure for ambient air, e.g. a cotton plug. The most commonly used flasks in this context are Erlenmeyer flasks, such as narrow-neck Erlenmeyer flasks according to ISO 1773 or wide-neck Erlenmeyer flasks according to ISO 24450. However, the oxygen transfer into the solution is limited in this setup. Typically, the oxygen content of the solution is high at its interface to the air, but the transfer of oxygen from this oxygen rich layer to the rest of the solution is slow and inefficient. Furthermore, the ratio of surface area to culture volume as well as the shaking speed and shaking diameter play a crucial role for oxygen transfer. To improve the oxygen transfer, baffled flasks have been developed. A baffled flask has a shape similar to the one of a corresponding Erlenmeyer flask, but with baffles at its bottom inner surface or at the side wall inner surface. When the baffled flask is shaken, the baffles increase mixing within the solution and hence improve the oxygen transfer from the oxygen rich layer to the rest of the solution. However, the shape of the baffles can vary due to the production process, in particular, for flasks made of glass, and so varies the oxygen transfer rate, resulting in undesirable variations when cultivating microorganisms. Moreover, the production of baffled flasks is technically more complicated than the production of a corresponding Erlenmeyer flask (without baffles), and consequently their price is high, ranging from about 5 to 10 times the price of the corresponding Erlenmeyer flask.

SUMMARY

In view of the technical problems laid out above, there is a need for improvements related to flasks, such as flasks applied for cultivating microorganisms. This objective is achieved with an inlay for a flask according to claim 1, and with a method for inserting an inlay into a flask according to claim 13. The dependent claims refer to advantageous embodiments.

According to a first aspect, an inlay for a flask comprises a bottom portion, a side portion, an intermediate portion, and a baffle element. The bottom portion comprises a downward-facing or downward-and-outward-facing first surface for abutting a bottom inner surface of the flask. The side portion comprises an outer surface for abutting a side inner surface of the flask, wherein the outer surface faces outwards with respect to a vertical reference line intersecting the inlay. The intermediate portion mechanically connects the bottom portion and the side portion. The baffle element extends away from the bottom portion, from the side portion, and/or from the intermediate portion for extending into an inner volume of the flask. An inner angle between the first surface and the outer surface is at least 50°, wherein the inner angle refers to an angle on the side of the vertical reference line in a vertical cross section through the inlay. The inlay comprises a first flexible material adapted to allow for bending said side portion inwards. The inlay is adapted to allow for folding the inlay with respect to a horizontal crease line to insert the inlay into the flask. The inlay comprises, along a vertical plane comprising the horizontal crease line, a second flexible material to allow for said folding.

The respective inlay provides baffle elements (which may alternatively referred to as stirring elements) to a flask, such as an Erlenmeyer flask, as for example, also a baffled flask does. Consequently, the inlay improves the mixing within the flask, and thus the oxygen transfer rate into a solution contained in the flask when the flask is shaken.

Compared to the baffled flask, the inlay can be fabricated much more easily, for example by molding, and, consequently, its price is much lower.

The accuracy of the produced (e.g., by molding) baffle elements is much higher than the accuracy in the production of baffled flasks, in particular, in the production of baffled flasks made from glass. This improves the reproducibility of the microorganism culture.

Various inlays with different sizes, inner angles, or baffle elements, can easily and economically be provided, such that a user may economically keep a stock of respective inlays and select the best one for the needs of his current microorganism culture.

The inlay can be removed from the flask when no longer needed, and both the flask and the inlay can be reused, for example, in another combination of flask and inlay.

According to an alternative embodiment, an inlay for a flask comprises a bottom portion, a side portion, an intermediate portion, and a baffle element. The bottom portion comprises a downward-facing bottom surface for providing a force-fit connection to a bottom inner surface of the flask. The side portion comprises an outer surface for providing a force-fit connection to a side inner surface of the flask. The outer surface faces outwards with respect to a vertical reference line intersecting the inlay. The intermediate portion mechanically connects the bottom portion and the side portion. The baffle element extends away from the bottom portion, from the side portion, and/or from the intermediate portion for extending into an inner volume of the flask. The inlay comprises a first elastomer for providing the force-fit connection of the downward-facing bottom surface to the bottom inner surface of the flask and the force-fit connection of the outer surface to the side inner surface of the flask. An inner angle between the bottom surface and the outer surface is at least 50°, wherein the inner angle refers to an angle on the side of the vertical reference line in a vertical cross section through the inlay. The first elastomer allows for bending said side portion inwards against an elastic restoration force, said restoration force promoting said force-fit connection. The inlay is adapted to allow for folding the inlay with respect to a horizontal crease line. The inlay comprises, along a vertical plane comprising the horizontal crease line, a second elastomer, wherein the second elastomer is adapted to allow for said folding, and is adapted to unfold the inlay upon said folding, for inserting the inlay into the flask.

In some embodiments, a ratio of a height of the inlay along the vertical direction and a maximum width of the inlay in a horizontal direction is at most 0.5, or at most 0.4, or at most one third.

A height of the inlay may be at most 10 cm, or at most 6 cm, or at most 5 cm, or at most 4 cm.

This facilitates easy and reliable folding to a sufficiently small size to insert the inlay into the flask.

A height of the inlay may be at least 0.5 cm, or at least 0.75 cm, or at least 1 cm.

Material compositions of the first flexible material and the second flexible material may be identical.

The inlay may be an integral part, such as an integral part formed by molding and/or an integral part composed of a flexible material providing the first flexible material and/or the second flexible material.

Corresponding embodiments facilitate mass production, as the inlay may be produced in large numbers by molding, in particular in a single molding step.

A surface of the inlay may be hydrophilic.

Alternatively, or in addition, a surface of the bottom portion and/or of the side portion and/or of the intermediate portion and/or of the baffle element and/or of the first flexible material and/or of the second flexible material may be hydrophilic.

The hydrophilic surface(s) improves biocompatibility and also improves the wettability of the inlay, hence improving the oxygen transfer further.

The intermediate portion may be arranged between the bottom portion and the side portion.

The intermediate portion or an outward-facing surface of the intermediate portion may extend from the outer surface to the first surface, in particular, from a bottom edge of the outer surface and/or to an outer edge of the first surface.

In some embodiments, the outward-facing surface of the intermediate portion comprises an orientation with a downward component and/or with an outward component.

Alternatively, or in addition, the outward-facing surface of the intermediate portion may comprise a convex shape, in particular, with a radius in a range from 6 mm to 6 cm.

In corresponding embodiments, the intermediate portion and/or its outward-facing surface is adapted to abut the flask at the transition between its bottom inner surface and its side inner surface, ideally flush.

The first flexible material may be a first elastomer.

According to some embodiments, the first elastomer is adapted to promote a force-fit connection of the first surface to the bottom inner surface of the flask and/or to promote a force-fit connection of the outer surface to the side inner surface of the flask.

According to some embodiments, the first elastomer is adapted to, upon the bending the side portion inwards, provide an elastic restoration force against the bending, said restoration force promoting said force-fit connection of the side portion to the side inner surface of the flask and/or of the first surface to the bottom inner surface of the flask.

The second flexible material may be a second elastomer.

According to some embodiments, the second elastomer is adapted to allow for said folding, and is adapted to unfold the inlay upon said folding.

In corresponding embodiments, the inlay is securely held in place using the force-fit connection(s) provided by the elastomer(s). This connection is detachable, so that the inlay and the flask may be separated from each other after usage together, and may be reused separately.

The downward-facing or downward-and-outward-facing first surface may be a downward-facing bottom surface of the bottom portion.

According to some embodiments, in a horizontal plane intersecting the bottom portion and/or the first surface and/or the intermediate portion, a shape of the bottom portion and/or a shape of the first surface and/or a shape of the intermediate portion is a ring segment or a ring.

According to some embodiments, in a horizontal plane intersecting the bottom portion and/or the first surface, a shape of the bottom portion and/or a shape of the first surface is a ring segment or a ring. A width of the ring segment or of the ring may be at least 2 millimeters, or at least 4 mm, or at least 6 mm.

The bottom portion and/or the first surface may comprise an opening, in particular, comprising its center/their centers or centered in its center/their centers.

The opening may have a width or a diameter of at least 1 cm or of at least 2 cm or of at least 3 cm.

The opening may have a circular shape and/or the opening may be centered in the first surface.

In corresponding embodiments, the ring-shape or the opening facilitates inserting the inlay into the flask, and improves the flush abutting of the downward-facing or downward-and-outward-facing first surface and the bottom inner surface of the flask.

The inlay may be an integral part composed of an elastomer material providing the first elastomer and the second elastomer.

The first elastomer and/or the second elastomer may comprise or may be rubber or silicone.

Material compositions of the first elastomer and the second elastomer may be identical.

The intermediate portion and/or the side portion may comprise or may be composed of the second elastomer.

The bottom portion may comprise or may be composed of the first elastomer.

The side portion and/or the intermediate portion may comprise or may be composed of the first elastomer.

The baffle element may comprise or may be composed of the first elastomer.

A thickness of the bottom portion, in particular along the vertical direction, may be at most 6 mm, or at most 5 mm, or at most 4 mm.

A thickness of the side portion, in particular along a radial direction with respect to the vertical reference line, may be at most 6 mm, or at most 5 mm, or at most 4 mm.

A thickness of the intermediate portion may be at most 6 mm, or at most 5 mm, or at most 4 mm.

Respective thicknesses ensure that the material is indeed flexible, for example when an elastomer material or a suitable polymer material is used.

The first surface may be flat and/or may extend in a horizontal plane.

The inner angle may be at least 60°, or at least 70°, or at least 75°, or at least 80°, or at least 85°, or at least 90°, or more than 90°, or at least 91°, or more than 95°.

A height of the outer surface along the vertical direction may be at least 2 mm, or at least 4 mm, or at least 6 mm.

A width or a diameter of the inlay in the horizontal direction may be in a range from 4 cm to 30 cm.

The vertical reference line may extend through a center of the inlay and/or of the bottom portion and/or of the side portion and/or of the intermediate portion.

The horizontal crease line may extend through the bottom portion and/or through the intermediate portion and/or through the first surface, in particular, through a center thereof.

The vertical cross section and/or the vertical plane may comprise the vertical reference line.

According to some embodiments, the outer surface or at least a section of the outer surface extends along a side of a reference cylinder, wherein an axis of the reference cylinder is aligned with the vertical reference line, and wherein, optionally, the first surface and/or the bottom portion and/or the intermediate portion and/or the baffle element is/are fully comprised in the reference cylinder.

According to some embodiments, the bending the side portion inwards bends the side portion towards the vertical reference line and/or reduces the inner angle, wherein, optionally, the elastic restoration force acts to bend the side portion away from the vertical reference line and/or to increase the inner angle.

The baffle element may comprise or be composed of an elastomer.

The baffle element may extend upwards from the bottom portion.

The baffle element may extend inwards from the side portion.

The baffle element may be recessed above the horizontal crease line.

The inlay may further comprise a second opening adapted for receiving an optode or for permitting a line of sight from below the flask to the inner volume of the flask, in particular, wherein the second opening has an extrusion shape corresponding to an extrusion of a base in a horizontal plane along the vertical direction.

The inlay may further comprise a recess adapted to receive a feeding pill or a feeding cartridge or a buffer pill or a buffer cartridge, in particular, wherein the recess faces upwards or inwards, such as from the bottom portion and/or from the intermediate portion.

The inlay may further comprise a light-emitting diode mounted to the inlay, in particular, to the bottom portion and/or to the intermediate portion.

The light-emitting diode is particularly beneficial for cultivating phototrophic organisms such as algae.

The flask may be an Erlenmeyer flask, in particular a wide-neck or a narrow-neck Erlenmeyer flask, such as a narrow-neck Erlenmeyer flask according to ISO 1773 or a wide-neck Erlenmeyer flask according to ISO 24450 or an Erlenmeyer flask according to DIN 4797.

According to a second aspect, a method is provided for inserting an inlay into a flask. The inlay comprises a second flexible material and a baffle element. The method comprises folding the second flexible material with respect to a crease line; aligning the crease line parallel to an axis of the flask; inserting the folded inlay into the flask with the crease line aligned with the axis of the flask; and unfolding, unfolding the second flexible material, the inlay in the flask, such that a downward-facing or downward-and-outward-facing first surface and/or an outer surface of the inlay abuts an inner surface of the flask, and that the baffle element extends into an inner volume of the flask.

The second flexible material may be a second elastomer. The second elastomer may promote the unfolding the inlay in the flask.

The inlay may be unfolded by the second elastomer such that the crease line is orientated parallel to a bottom surface of the flask and/or orthogonal to the axis of the flask.

According to some embodiments, the inlay is unfolded such that the inlay is fully positioned below a neck portion of the flask.

The method may further comprise fixing the inlay in the flask and/or removing a section of the inlay in the flask, such as by etching or ashing.

According to some embodiments, the inlay comprises a bottom portion comprising the first surface, a side portion comprising the outer surface, an intermediate portion mechanically connecting the bottom portion and the side portion, and a first flexible material, such as a first elastomer, and the unfolding comprises: arranging the first surface to abut a bottom inner surface of the flask; and arranging the outer surface to abut a side inner surface of the flask.

In embodiments with the first elastomer, the method may further comprise providing, by the first elastomer, a force-fit connection of the first surface to the bottom inner surface of the flask and/or a force-fit connection of the outer surface to the side inner surface of the flask.

BRIEF DESCRIPTION OF THE DRAWINGS

The techniques of the present disclosure and the advantages associated therewith will be best apparent from a description of exemplary embodiments in accordance with the accompanying drawings, in which.

DETAILED DESCRIPTION

Figure 1A:
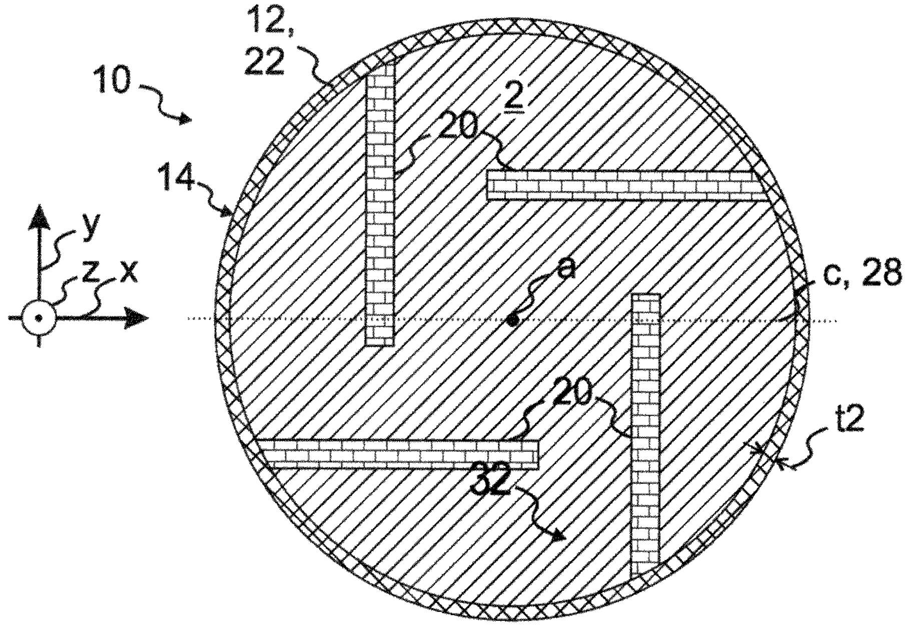
FIG. 1*a* is a top view of an inlay according to a first embodiment.
Figure 1B:
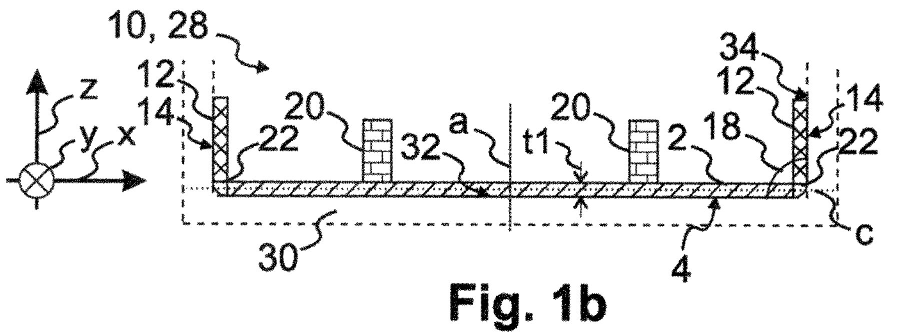
FIG. 1*b* is a sectional view of the inlay according to the first embodiment.

FIG. 1*a*, FIG. 1*b* show an inlay 10 according to a first embodiment. FIG. 1*a* is a top view, and FIG. 1*b* is a cross-sectional view along the vertical x, z plane 28 comprising the line c in FIG. 1*a*. In FIG. 1*b*, a bottom portion of a flask 30 (not shown in FIG. 1*a*) is indicated by dashed lines.

The inlay 10 comprises a bottom portion 2 and a side portion 12. An intermediate portion 22, which, in the depicted embodiment, is the edge between the bottom portion 2 and the side portion 12, and connects the portions 2, 12.

The bottom portion 2 has a first surface 4, adapted to abut a bottom inner surface 32 of a flask 30 (not shown in FIG. 1*a*). In the depicted embodiment, the first surface 4 faces downwards, but in other embodiments, it is a downward-and-outward-facing surface 4 (see FIG. 3*d*).

The side portion 12 has an outer surface 14, which is adapted to abut a side inner surface 34 of the flask 30.

The inner angle 18 between the first surface 4 and the outer surface 14 is selected according to the shape of a flask 30, that the inlay 10 is to be inserted into, and amounts to at least 50°, and preferably at least 70° to implement an inlay 10 for an Erlenmeyer flask.

Baffle elements 20 (stirring elements 20) in the form of fins 20 extend upwards from the bottom portion 2. In alternative embodiments, see FIG. 8*a*, FIG. 8*b*, FIG. 8*c*, FIG. 8*d*, FIG. 8*c*, the baffle elements 20 extend inwards from the side portion 12.

Where the vertical plane 28 intersects the inlay 10, the inlay comprises a (first) flexible material. Consequently, the inlay 10 can be folded along the line c. In this sense, line c serves as a crease line.

The side portion 12 of the inlay 10 can be bent inwards towards the axis a. For this purpose, the bottom portion 2 in the vicinity of the intermediate portion 22, the intermediate portion 22, and/or the side portion 12 comprises a flexible material.

In the embodiment depicted in FIG. 1*a*, FIG. 1*b*, the outer contour of the bottom portion 2 as well as the outer contour of the side portion 12 is a full circle, i.e., in the top view of FIG. 1*a*. In alternative embodiments (not shown), this full circle is interrupted. For example, the height of the side portion 12 and/or of the intermediate portion 22 and/or of the baffle element(s) 20 may be reduced above the crease line c or the respective element may be absent above the crease line c to facilitate easier folding with respect to the crease line c. In alternative embodiments (not shown), the outer contour of the bottom portion 2 as well as the outer contour of the side portion 12 is a square or a rectangle, i.e., in a top view.

Thicknesses t1, t2 of the bottom and the side portions 2, 12, respectively, are preferably no more than 6 mm, 5 mm, or 4 mm, to ensure that the material of the respective portion is flexible.

Figure 2A:
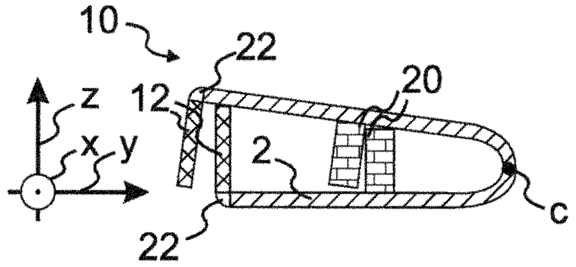
FIG. 2*a* is a sectional view of an inlay according to another embodiment.
Figure 2B:
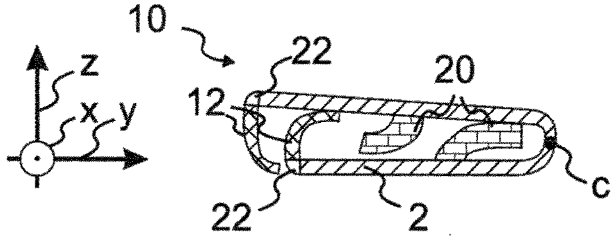
FIG. 2*b* is a sectional view of an inlay according to another embodiment.

FIG. 2*a*, FIG. 2*b* illustrate the folding of the inlay 10, giving cross sectional views of folded inlays according to different embodiments.

The inlay 10 of FIG. 2*a* comprises rigid baffle elements 20. The rigid baffle elements 20 may be advantageous in some embodiments to ensure a high oxygen transfer rate.

The inlay 10 of FIG. 2*b* comprises flexible baffle elements 20, i.e., baffle elements 20 comprising a flexible material. Advantageously, in this embodiment, the inlay 10 can be folded to a smaller height (as compared to the inlay 10 of the embodiment depicted in FIG. 2*a*). This makes inserting the inlay 10 into a flask easier, faster, and more reliable.

FIG. 3*a*, FIG. 3*b*, FIG. 3*c*, FIG. 3*d* illustrate various embodiments of the inlay 10 for different flasks 30.

Before going into the details of the individual embodiments, common properties of all the depicted embodiments will be described. These do not only apply to the embodiments of FIG. 3*a*, FIG. 3*b*, FIG. 3*c*, FIG. 3*d*, but as well to the other embodiments of this description.

In some embodiments, the inlay 10 is fixed in the flask 30, i.e., using a fixing element such as a glue or a resin. In corresponding embodiments, the first and/or second flexible material can be selected from a wide range of materials, including plastics, for as long as they are sufficiently thin to be flexible and allow for a bending with respect to the crease line c (see FIG. 2*a*, FIG. 2*b*) by more than 90°. The first and/or second flexible material can as well be an elastomer, such as silicone or rubber.

However, preferably, the inlay 10 is adapted to be held in place in the flask 10 using force-fit connections, i.e., a force-fit connection of the first surface 4 to the bottom inner surface 32 of the flask and/or a force-fit connection of the outer surface 14 to the side inner surface 34 of the flask 30. For this purpose, the first and/or second flexible material is/are an elastomer material.

The second elastomer material, along the crease line c, provides a restoration force against the folding of the inlay 10 with respect to the crease line c. In other words, when the force which caused the folding is released, the inlay 10 is unfolded by the second elastomer, or by the restoration force it provides, respectively. This pushes the outer surface 14 against the side inner surface 34 of the flask 30, and the first surface 4 against the bottom inner surface 32 of the flask 30, promoting said force-fit connections.

The first elastomer material, comprised in the side portion 12, the intermediate portion 22, and/or the bottom portion 2 in the vicinity of the intermediate portion 22, provides an elastic restoration force against the bending inwards of the side portion 12. Consequently, this restoration force pushes the outer surface 14 against the side inner surface 34 of the flask 30, and the first surface 4 against the bottom inner surface 32 of the flask, further promoting said force-fit connections.

The advantage of the embodiments adapted to provide the force-fit connection(s) over the ones fixed in the flask 30 is rooted in the force-fit connection(s) being detachable. Consequently, the inlay 10 can be removed from the flask 30 without damaging or destroying it, and can be reused after cleaning or in another flask 30.

The first and/or second elastomer material is/are typically rubber or silicone. Those also offer the advantage that the flask 30 can be autoclaved with the inlay 10 inside.

Inlays 10 for being fixed to the flask 30 have inner angles 18 corresponding to the inner angle between the bottom inner wall 32 and the side inner wall 34 of the respective flask 30.

Inlays 10 for force-fit connection(s) to the flask 30 have inner angles 18 slightly larger than the inner angle between the bottom inner wall 32 and the side inner wall 34 of the respective flask 30. A difference of at least 1° is preferred, for example a difference of 1° or 2° has proven sufficient.

Figure 3A:
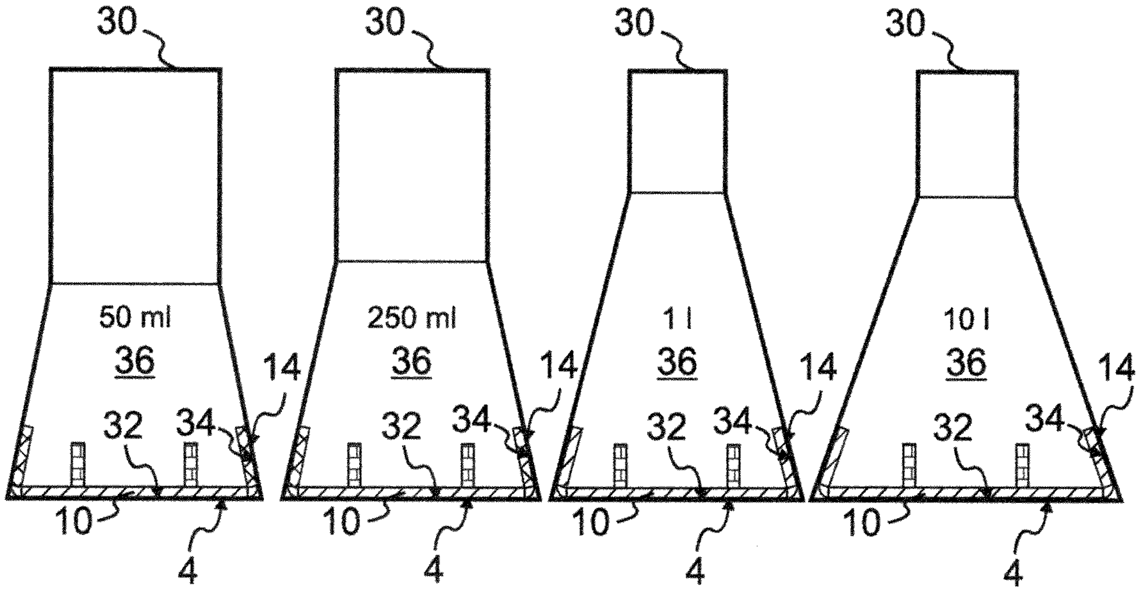
FIG. 3*a* is sectional views of inlays according to other embodiments.

FIG. 3*a* illustrates inlays 10 for wide-neck Erlenmeyer flasks 30 according to ISO 24450. The inner angles between the bottom inner walls 32 and the side inner walls 34 of those Erlenmeyer flasks 30 are in the range from 71-79°, with generally larger angles for smaller flasks. The inlay 10 for the wide-neck Erlenmeyer flasks 30 has an inner angle 18 of at least 70°.

Figure 3B:
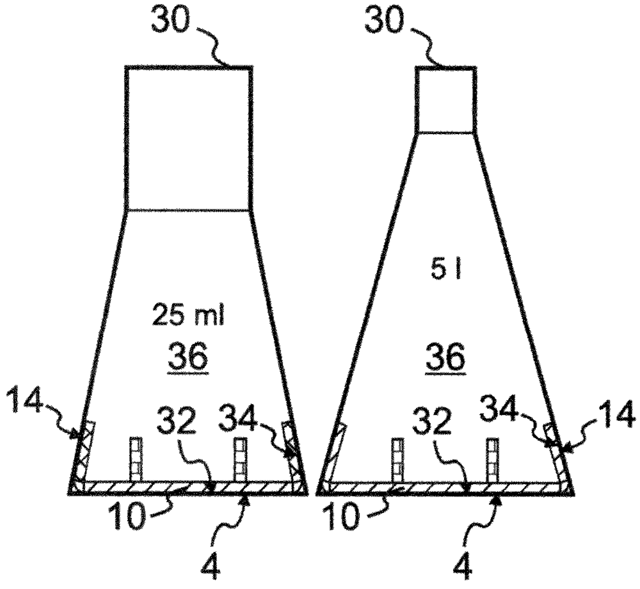
FIG. 3*b* is sectional views of inlays according to other embodiments.

FIG. 3*b* illustrates inlays 10 for narrow-neck Erlenmeyer flasks 30 according to ISO 1773. The inner angles between the bottom inner walls 32 and the side inner walls 34 of those Erlenmeyer flasks 30 are in the range from 75-79°, with generally larger angles for smaller flasks. The inlay 10 for the narrow-neck Erlenmeyer flasks 30 has an inner angle 18 of at least 75°.

Figure 3C:
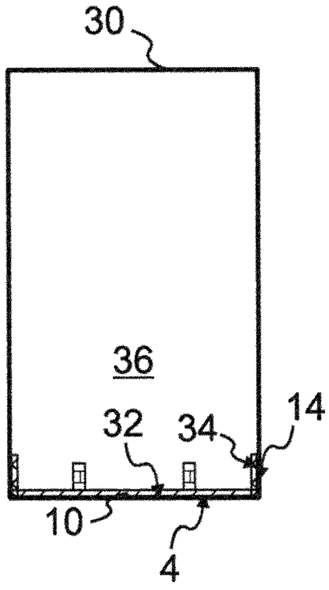
FIG. 3*c* is a sectional view of an inlay according to another embodiment.

FIG. 3*c* illustrates an inlay 10 for a flask 30 with vertical inner side walls, i.e., with an inner angle 18 of 90° between the bottom inner wall 32 and the side inner walls 34 of the flask 30.

Figure 3D:
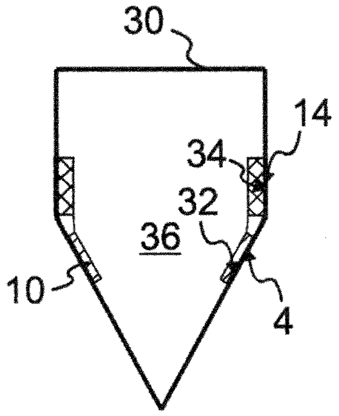
FIG. 3*d* is a sectional view of an inlay according to another embodiment.

FIG. 3*d* illustrates an inlay 10 for a flask 30 typically used with a centrifuge (not shown). This type of flask 30 has an inner angle 18 in the range from 95° to 120° between its bottom inner wall 32 and its side inner walls 34.

Fernbach flasks (not shown) have inner angles between 50° and 70°. An inlay (not shown) for a Fernbach flask has an inner angle 18 of at least 50°.

Figure 4A:
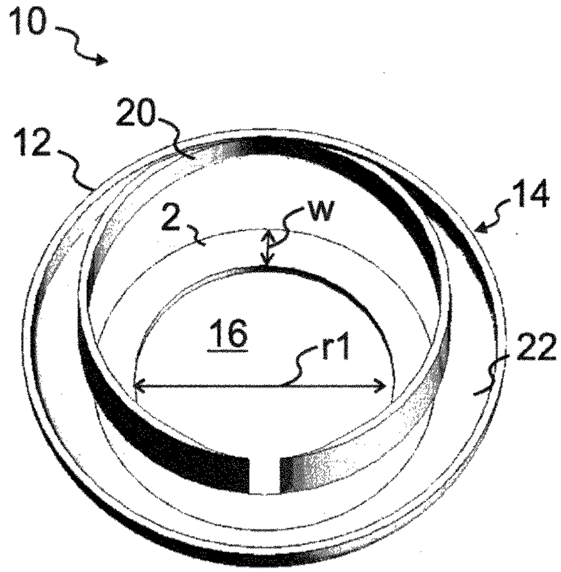
FIG. 4*a* is a perspective view of an inlay according to another embodiment.
Figure 4B:
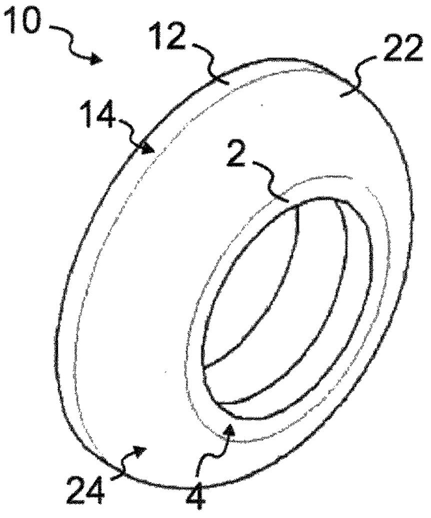
FIG. 4*b* is another perspective view of the inlay according to the embodiment of FIG. 4*a;*
Figure 4C:
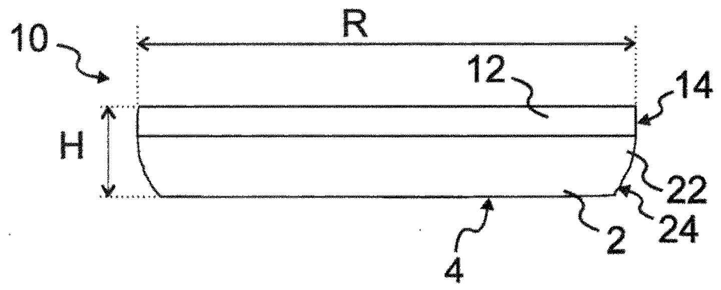
FIG. 4*c* is a side view of the inlay according to the embodiment of FIG. 4*a*, FIG. 4*b;*

FIG. 4*a*, FIG. 4*b*, FIG. 4*c* illustrate another embodiment of the inlay 10. FIG. 4*a*, FIG. 4*b* give different perspective views of the inlay 10 according to the embodiment. FIG. 4*c* is a side view.

The inlay 10 of FIG. 4*a*, FIG. 4*b*, FIG. 4*c* is formed with an opening 16.

The opening 16 makes it easier to fold the inlay 10 and it also improves the fit of the inlay 10 to the flask 30, in particular of the first surface 4 to the bottom inner surface 32 of the flask 30. Moreover, the opening 16 reduces the amount of material needed to fabricate the inlay 10.

The opening 16 may also be formed with any of the other embodiments.

The opening 16 comprises the center of the first surface 4. In the depicted embodiment, it is centered, but it may also be arranged slightly off-center. In the depicted embodiment, the opening 16 has a circular cross-section, but alternative cross-sections are possible, for as long as the amount of material of the bottom surface 2 is reduced sufficiently to improve the folding and the fit to the flask 30. A diameter r1 (FIG. 4*a*) of the opening 16 in the range from 1-3 cm has proven useful for this purpose. In case of a non-circular cross section, a width thereof is selected in the same range.

The intermediate portion 22 of the inlay 10 has an outward-facing surface 24, with a convex (i.e., outward-curved) shape, facing downward and outward. The curvature of the outward-facing surface 24 (FIGS. 4*b*, 4*c*) is matched to the curvature of a typical lab flask 30 at the transition from its bottom inner wall 32 to its side inner walls 34. More specifically, the curvature is in the range from 6 mm to 6 cm, matched to the respective curvature of Erlenmeyer flasks 30 according to ISO 1773 or ISO 24450.

A corresponding outward-facing surface 24 may also be formed on any of the other embodiments.

The diameter R (cf. FIG. 4*c*) of the inlay 10 is in the range of 4 to 30 cm, matched to the maximum inner diameter of Erlenmeyer flasks 30 according to ISO 1773 or ISO 24450. Typically, the diameter R is selected with a value of 1 to 5 mm larger than an inner diameter of the flask 30 at its widest position.

The height H (cf. FIG. 4*c*) of the inlay 10 is in the range from 0.5 cm to 10 cm, depending on the size of the flask. Within this range, a smaller height H improves the folding, whereas a larger height H improves the adhesion to the side inner wall of the flask 30. The range from 0.5 cm to 6 cm ensures the balancing of both properties.

The width w of the ring-shaped bottom portion of the inlay 10 is approximately 1 cm in case of an inlay for a 250 ml Erlenmeyer flask.

FIG. 5*a*, FIG. 5*b*, FIG. 5*c*, FIG. 5*d* illustrate a method for inserting an inlay 10 into a flask 30.

Figure 5A:
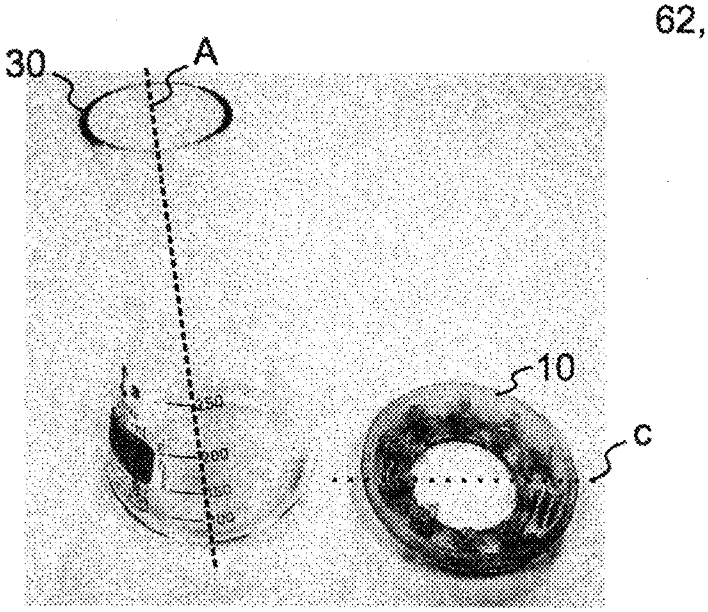
FIG. 5*a* illustrates a method for inserting an inlay into a flask according to an embodiment.

FIG. 5*a* shows the inlay 10 outside of the flask 30, as is the case at the beginning of the method. The flask 30 is an Erlenmeyer flask 30 with an axis A.

Figure 5B:
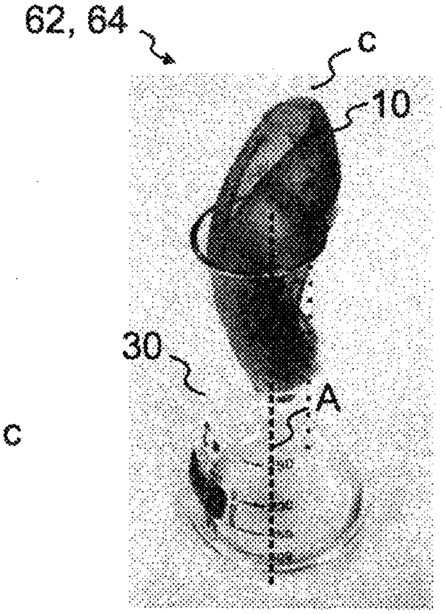
FIG. 5*b* further illustrates the method for inserting the inlay into the flask.

FIG. 5*b* shows the folding of the inlay 10 with respect to the crease line c.

FIG. 5*b* further shows that the inlay 10 with its crease line c is aligned with the axis A of the flask 30.

Figure 5C:
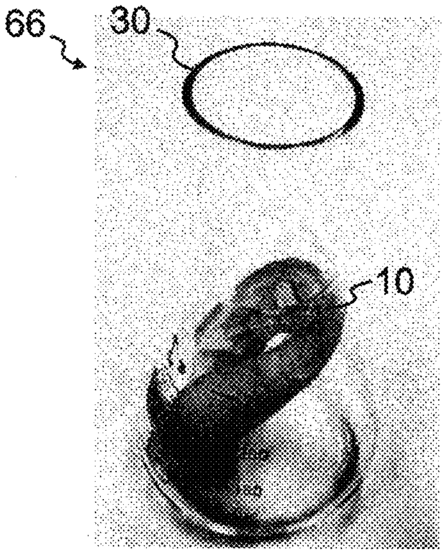
FIG. 5*c* further illustrates the method for inserting the inlay into the flask.

FIG. 5*c* shows the inlay 10 and the flask 30, after the inlay 10 has been inserted with its crease line c aligned with the axis A of the flask 30 (as depicted in FIG. 5*b*). The inlay 10 is arranged fully below the neck portion of the flask 30.

In FIG. 5*c*, the inlay 10 is being unfolded. In the depicted embodiment, the inlay 10 is an integral piece of elastomer, more specifically of silicone, formed by molding. As the forces applied to the inlay 10 during the insertion into the flask 30 (FIG. 5*b*) are released in FIG. 5*c*, the elastomer provides a restoring force driving the inlay 10 back into its original shape as depicted in FIG. 5*a*.

In alternative embodiments (not shown), the inlay 10 is not elastic, i.e., it does not comprise an elastomer. In corresponding embodiments, an additional action is required to unfold the inlay 10 inside of the flask 30. In other words, a machine, a tool or a worker grasps into the flask 30 and unfolds the inlay 10.

Figure 5D:
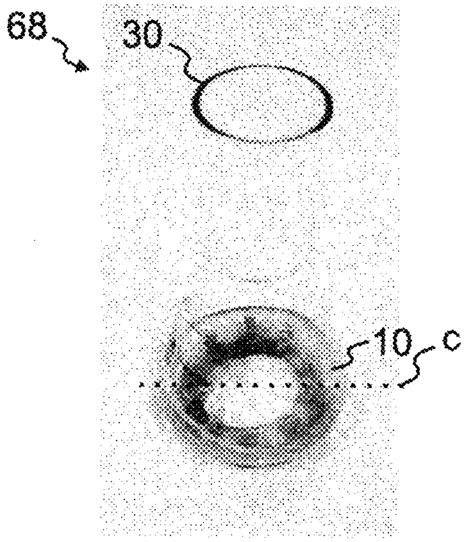
FIG. 5*d* further illustrates the method for inserting the inlay into the flask.

FIG. 5*d* shows the inlay 10 in its final state in the flask 30 after the unfolding.

In some embodiments (not shown) the inlay 10 is fixed in the flask 30, for example with glue. In yet other embodiments (not shown) a portion of the inlay 10 is removed, by etching or ashing (i.e., heating the flask 30 to a temperature above a decomposition temperature of the material of the inlay 10).

Figure 6:
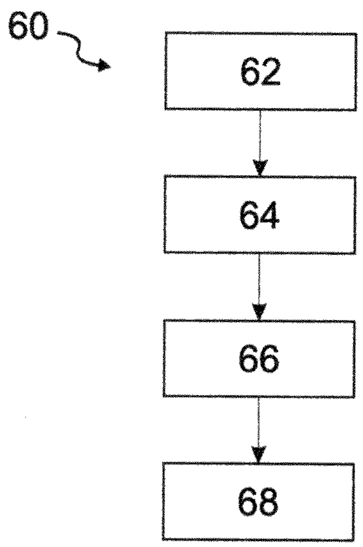
FIG. 6 illustrates a method for inserting an inlay into a flask according to another embodiment.

FIG. 6 illustrates a method 60 for inserting an inlay 10 into a flask 30 according to an alternative embodiment. The inlay 10 comprises a second flexible material and a baffle element 20.

The method 60 begins with folding 62 the second flexible material with respect to a crease line c.

The method 60 continues with aligning 64 the crease line c parallel to an axis A of the flask 30.

The method 60 continues with inserting 66 the folded inlay 10 into the flask 30 with the crease line c aligned with the axis A of the flask 30.

The method further comprises unfolding 68, unfolding the second flexible material, the inlay 10 in the flask 30, such that a downward-facing or downward-and-outward-facing first surface 4 and/or an outer surface 14 of the inlay 10 abuts an inner surface 32, 34 of the flask 30, and that the baffle element 20 extends into an inner volume 36 of the flask 30.

FIG. 7*a*, FIG. 7*b*, FIG. 7*c*, FIG. 7*d*, FIG. 7*e* give perspective views of inlays 10 according to various embodiments with a baffle element 20 extending upwards from the bottom portion 2.

Figure 7A:
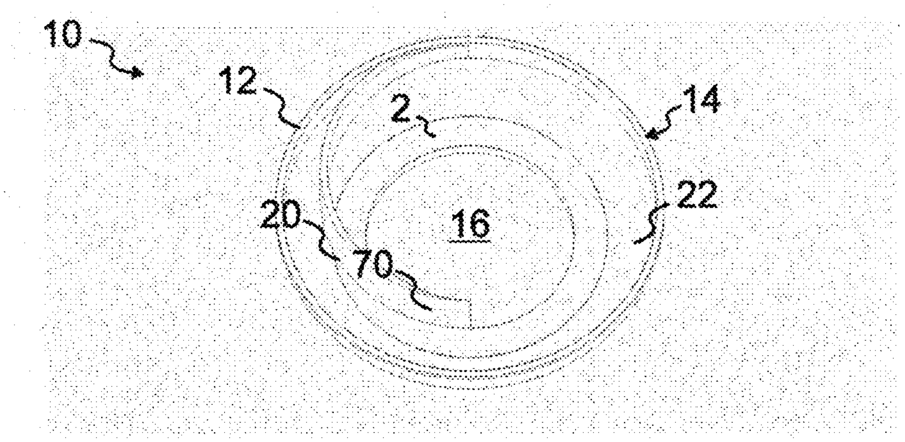
FIG. 7*a* is a perspective view of an inlay according to an embodiment with a baffle element extending upwards from a bottom portion.
Figure 7B:
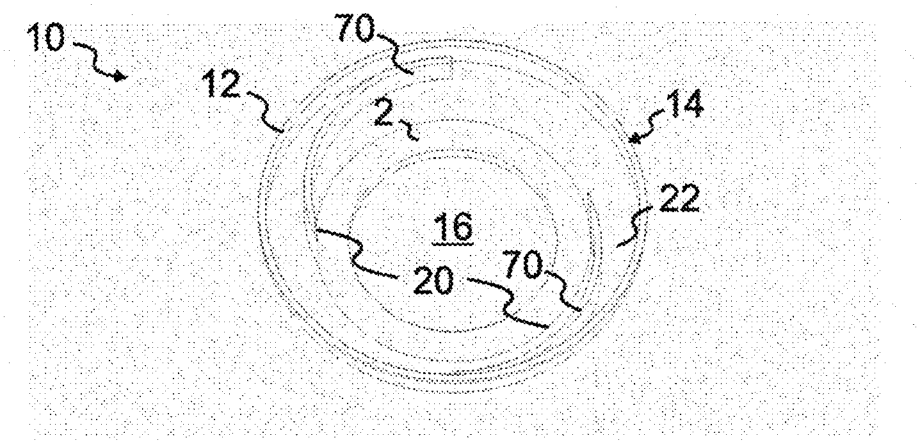
FIG. 7*b* is a perspective view of an inlay according to another embodiment with a baffle element extending upwards from a bottom portion.
Figure 7C:
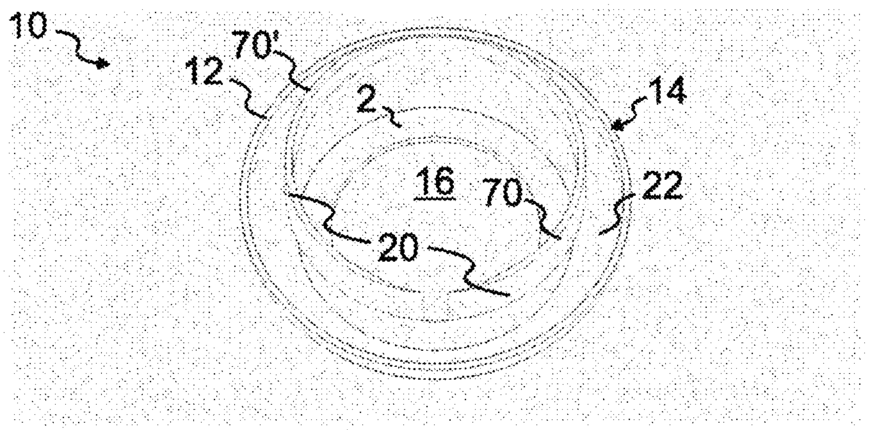
FIG. 7*c* is a perspective view of an inlay according to another embodiment with a baffle element extending upwards from a bottom portion.

In the embodiments of FIG. 7*a*, FIG. 7*b*, FIG. 7*c*, the baffle element 20 comprises a c-shaped, or half-moon-shaped element 70. The respective element has an extrusion shape, with a c-shaped, or half-moon-shaped horizontal basis in a horizontal plane. The extrusion refers to an extrusion along the vertical direction, resulting in the height of the respective baffle element 20.

The inlay 10 of FIG. 7*a* comprises a single c-shaped, or half-moon-shaped element 70.

The inlay 10 of FIG. 7*b* comprises two c-shaped, or half-moon-shaped elements 70, arranged opposite to each other, with an interruption along the azimuthal direction.

The inlay 10 of FIG. 7*c* comprises a single, extended c-shaped element 70' covering approximately 270° (i.e., more than 180°, and/or more than) 230° along the azimuthal direction. The c-shaped element 70' of FIG. 7*c* preferably comprises an interruption along the azimuthal direction.

Figure 7D:
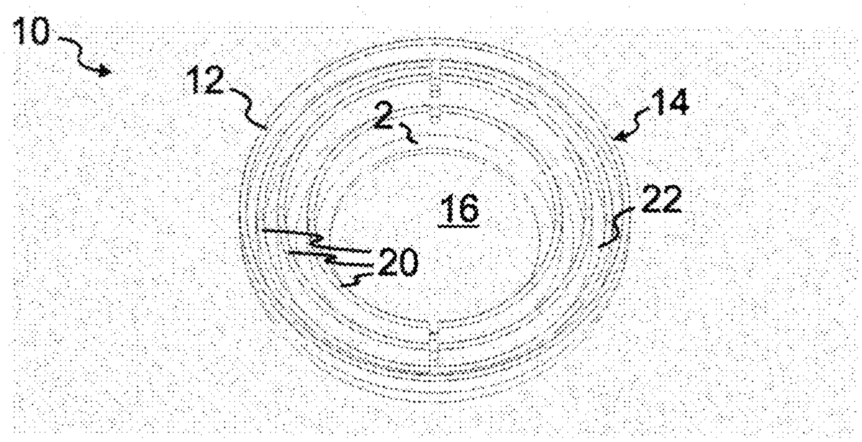
FIG. 7*d* is a perspective view of an inlay according to another embodiment with a baffle element extending upwards from a bottom portion.
Figure 7E:
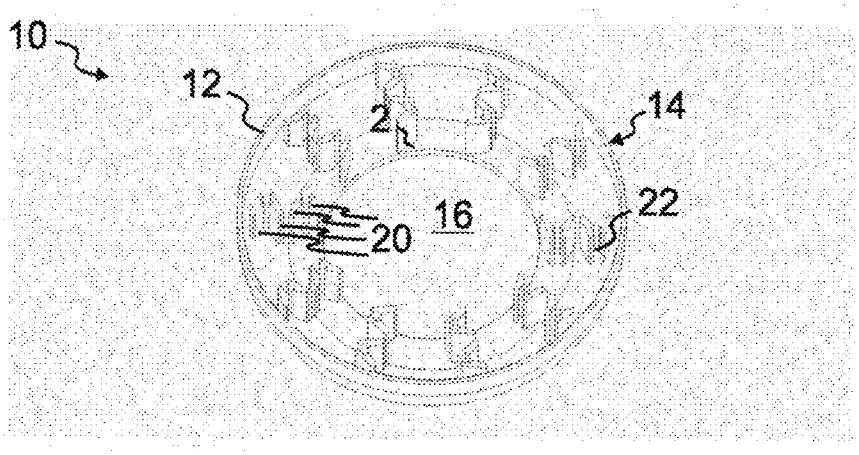
FIG. 7*e* is a perspective view of an inlay according to another embodiment with a baffle element extending upwards from a bottom portion.

In the embodiments of FIG. 7*d*, FIG. 7*e*, the baffle element 20 comprises fins extending upwards from the bottom portion 2. The fins have extrusion shapes with bases in a respective horizontal plane.

At least 4 or at least 8 or at least 10 fins are preferable. The embodiment of FIG. 7*d* comprises 12 fins. The embodiment of FIG. 7*e* comprises 40 fins.

Figure 8A:
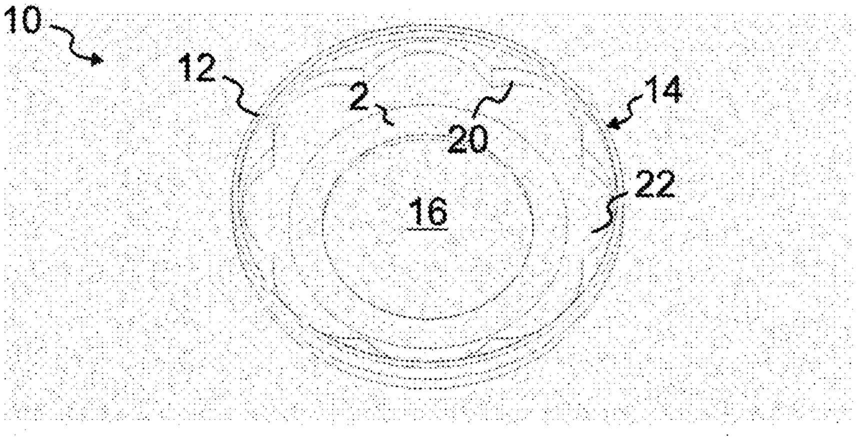
FIG. 8*a* is a perspective view of an inlay according to an embodiment with a baffle element extending inwards from a side portion.
Figure 8B:
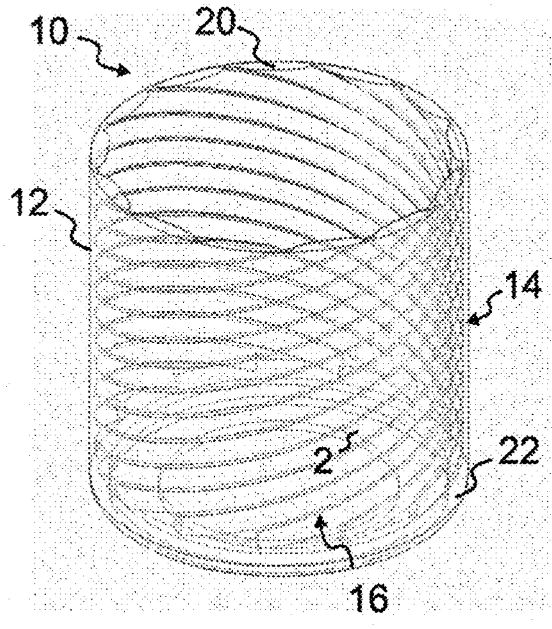
FIG. 8*b* is a perspective view of an inlay according to another embodiment with a baffle element extending inwards from a side portion.
Figure 8C:
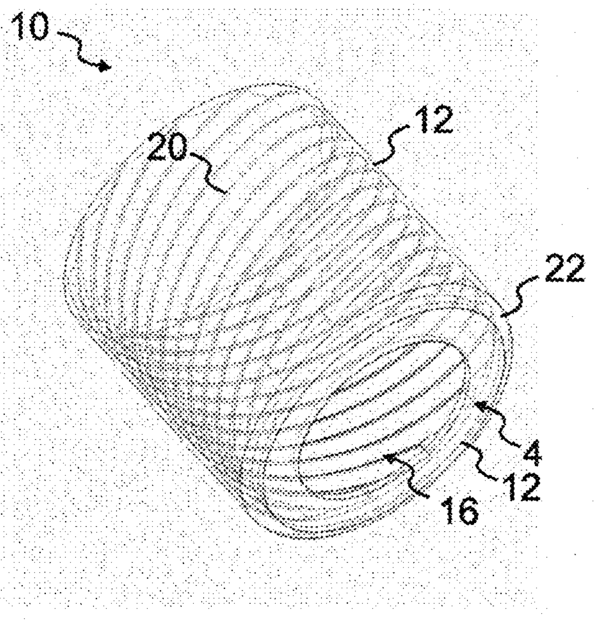
FIG. 8*c* is another perspective view of the embodiment of FIG. 8*b;*
Figure 8D:
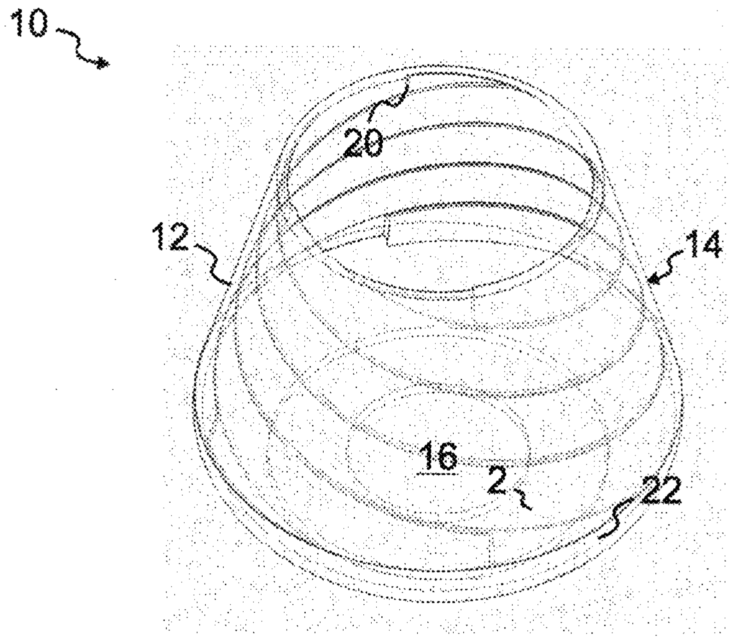
FIG. 8*d* is a perspective view of an inlay according to another embodiment with a baffle element extending inwards from a side portion.
Figure 8E:
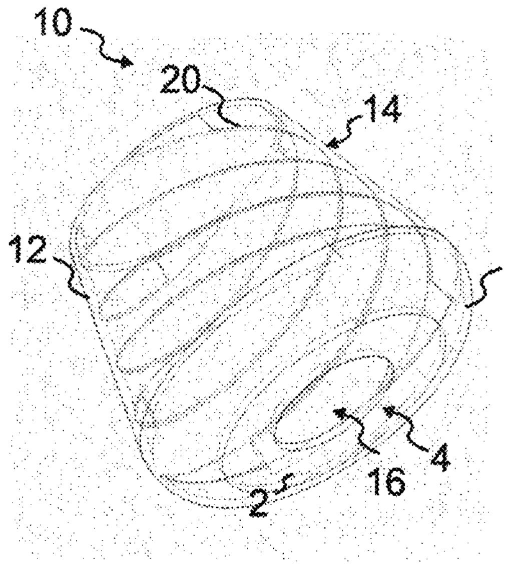
FIG. 8*e* is another perspective view of the embodiment of FIG. 8*d;*
Figure 8F:
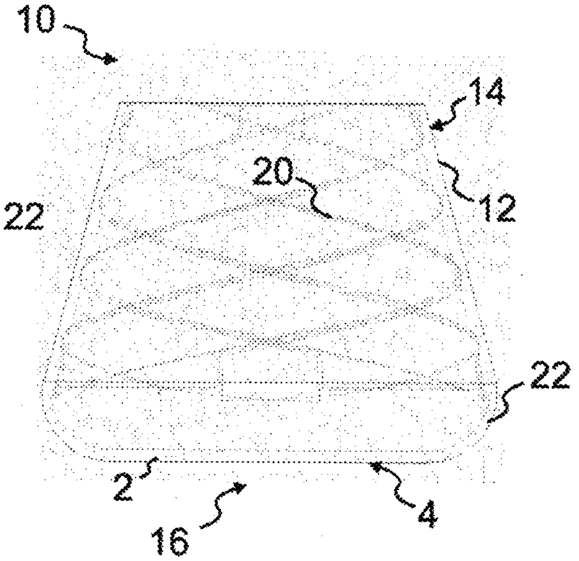
FIG. 8*f* is a cross-sectional view of the embodiment of FIG. 8*d* and FIG. 8*e;*

FIG. 8*a*, FIG. 8*b*, FIG. 8*c*, FIG. 8*d*, FIG. 8*e*, FIG. 8*f* illustrate inlays 10 according to three embodiments with a baffle element 20 extending inwards from the side portion 12. FIG. 8*b*, FIG. 8*c* refer to the same embodiment. FIG. 8*d*, FIG. 8*e*, FIG. 8*f* refer to the same embodiment.

The inlay of FIG. 8*a* has a baffle element 20 with an inner contour, i.e., in a horizontal plane, having a rosette-shape. The depicted baffle element 20 has an inner contour according to an 8-leaved rosette. However, an inner contour according to a 3-, 4-, 5-, 6-, 7- or more leaved rosette is alternatively possible.

The inlay 10 of FIG. 8*b*, FIG. 8*c* and the inlay 10 of FIG. 8*d*, FIG. 8*c*, FIG. 8*f* has a baffle element 20 with a shape of a screw extending along an inner surface of the side portion 12.

The inlay 10 of FIG. 8*b*, FIG. 8*c* is adapted for a flask 30 with vertical inner side walls 34.

The inlay 10 of FIG. 8*d*, FIG. 8*e*, FIG. 8*f* is adapted for an Erlenmeyer flask 30.

Figure 9A:
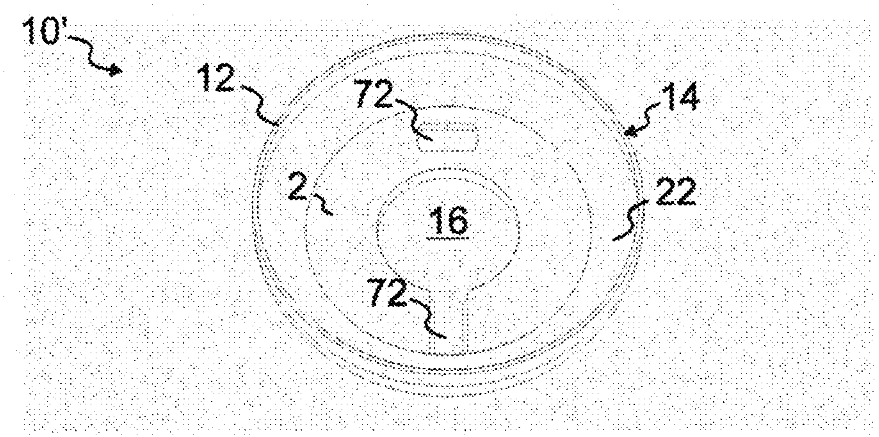
FIG. 9*a* is a perspective view of a body with second openings.
Figure 9B:
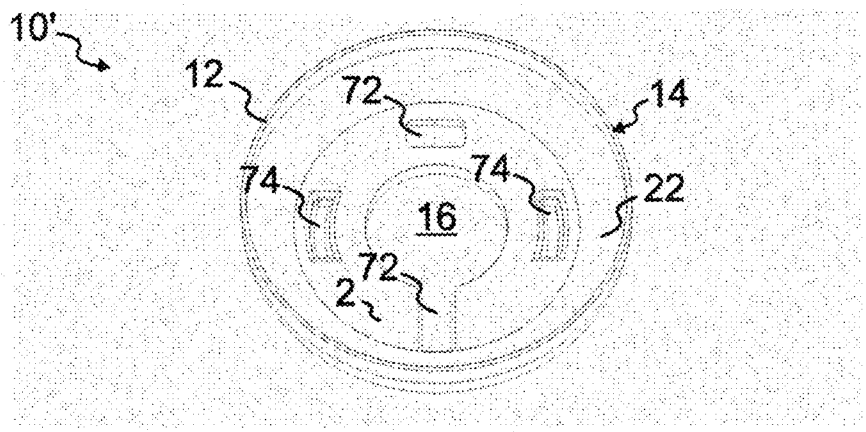
FIG. 9*b* is a perspective view of a body with second openings and recesses.
Figure 9C:
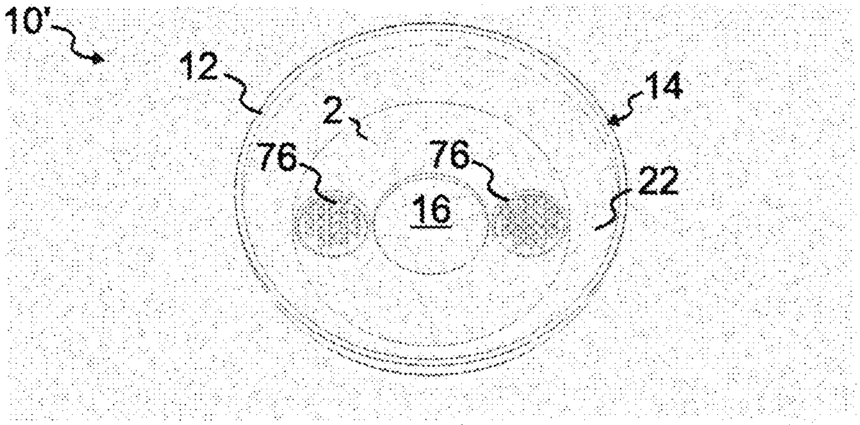
FIG. 9*c* is a perspective view of a body with light-emitting diodes.

FIG. 9*a*, FIG. 9*b*, FIG. 9*c* illustrate additional elements, such as a second opening 72, a recess 74, or a light-emitting diode 76, respectively.

The bodies 10' depicted in FIG. 9*a*, FIG. 9*b*, FIG. 9*c* are similar to the inlays 10 described above, with a bottom portion 2, a side portion 12, and an intermediate portion 22. However, as compared to the respective inlays, the bodies 10' miss respective baffle elements. The bodies 10' may be combined with any of the baffle elements 20 described above, e.g., with a baffle element 20 from FIG. 7*a*, FIG. 7*b*, FIG. 7*c*, FIG. 7*d*, FIG. 7*e*, or from FIG. 8*a*, FIG. 8*b*, FIG. 8*c*, FIG. 8*d*, FIG. 8*c*, FIG. 8*f* to form an inlay 10. In other words, the additional elements of FIG. 9*a*, FIG. 9*b*, FIG. 9*c* (i.e., second opening 72, recess 74, or light-emitting diode 76) can be formed on the inlay 10 according to any of the embodiments described above.

The body 10' of FIG. 9*a* is formed with (second) openings 72, with horizontal cross sections and orientations along the vertical directions, i.e., perpendicular to the cross section of the respective opening 72.

When an inlay 10 with the body 10' of FIG. 9*a* is inserted into a flask 30, the openings 72 can be used to shine light through them into the inner volume 36 of the flask from below the flask 30, e.g., at an optode (e.g. for measuring pH and/or dissolved oxygen) arranged in the flask 30. Furthermore, the light can also directly shine into the solution when no optodes are applied in flask 30 to measure biomass concentration, particle concentration and/or particle size, fluorescent markers and/or particles or other optical signals. Therefore, the openings 72 permit in situ analysis of the solution in the flask 30.

The body 10' of FIG. 9*b* is formed with recesses 74 for a feeding pill or a feeding cartridge, providing nutrients to the culture in flask 30 without the need for a pump. Alternatively, the recess may be used to provide a well-defined position for a buffer pill or a buffer cartridge for regulating the pH value of the solution.

When an inlay 10 with the body 10' of FIG. 9*b* is inserted into a flask 30, the recesses 74 can be used to keep a feeding pill or a feeding cartridge at a controlled position with a well-defined local environment. Therefore, the recesses 74 permit a more reproducible cultivation of the microorganisms in the solution because feeding pills or discs do not aggregate/stick together due to the fluid movement (aggregation causes variable surface area and hence variable nutrient release via diffusion of nutrient into the fluid).

The body 10' of FIG. 9*c* is formed with light-emitting diodes 76 mounted thereon.

When an inlay 10 with the body 10' of FIG. 9*c* is inserted into a flask 30, the light-emitting diodes 76 permit cultivating phototrophic microorganisms, e.g. algae, providing a high light intensity directly to the fluid and hence optimized cultivation conditions in comparison to shake flasks that are illuminated traditionally from above or beneath the flask through the absorbing glass material of the flask.

Figure 10:
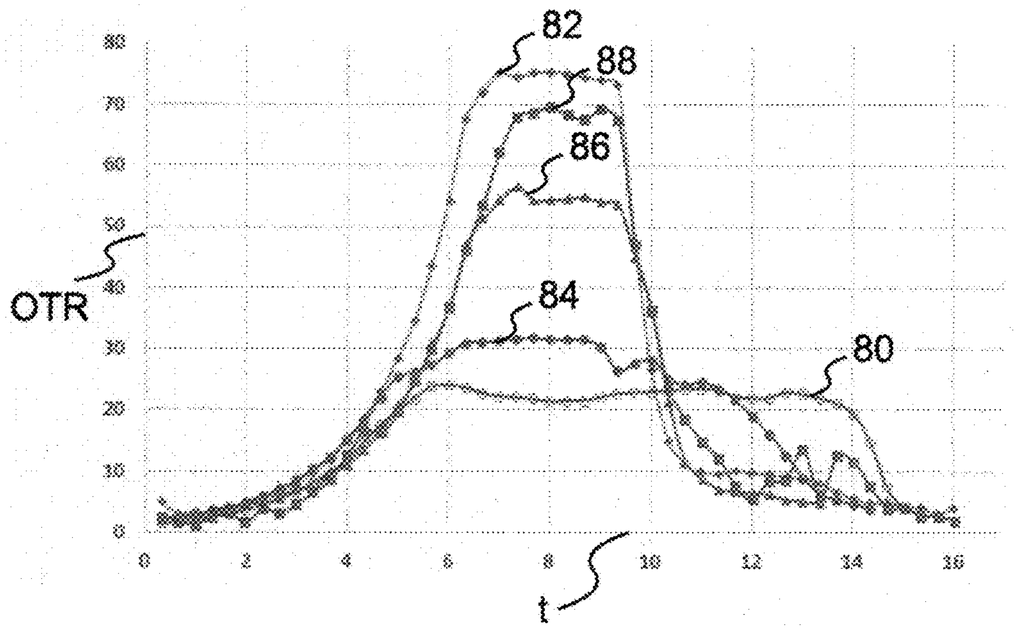
FIG. 10 illustrates oxygen transfer rates.

FIG. 10 compares the oxygen transfer rates OTR in mmol/(l*h) vs. time t in hours, for different flasks 30 with and without the inlay 10.

Oxygen transfer rate 80 is the one of a regular Erlenmeyer flask, such as a narrow-neck Erlenmeyer flask according to ISO 1773 or a wide-neck Erlenmeyer flask according to ISO 24450, i.e. without any baffle or baffle element. The oxygen transfer rate 80 is the lowest one measured with approx. 25 mmol/(l*h).

Oxygen transfer rate 82 is the one of a commercially available baffled flask. The oxygen transfer rate 82 is the highest one observed, thus providing a reference.

Oxygen transfer rate 84 is the one of an Erlenmeyer flask, wherein a body 10' without a baffle element 20 is inserted.

The oxygen transfer rate 84 is similarly low as the oxygen transfer rate 80 of the Erlenmeyer flask.

Oxygen transfer rates 86, 88 are the ones of Erlenmeyer flasks, wherein a respective inlay 10 is inserted. More specifically, oxygen transfer rate 88 uses the inlay 10 of FIG. 7*c*, and oxygen transfer rate 86 uses the inlay 10 of FIG. 7*e*. The oxygen transfer rates 86, 88 are significantly improved as compared to the oxygen transfer rate 80 of the Erlenmeyer flask or to the oxygen transfer rate 84 of the body 10'.

To summarize FIG. 10, the inlay 10 with the baffle element 20 improves the oxygen transfer rate OTR to a degree similar to the one of a baffled flask.

LIST OF REFERENCE SIGNS

10 inlay
30 flask
2 bottom portion of inlay
4 downward-facing or downward-and-outward-facing first surface
12 side portion of inlay
14 outer surface
22 intermediate portion of inlay
20 baffle element
a reference line
18 inner angle
c crease line
28 vertical plane
t1 thickness of bottom portion
t2 thickness of side portion
32 bottom inner surface of the flask
34 side inner surface of the flask
36 inner volume of the flask
16 opening
24 outward-facing surface of the intermediate portion of inlay
r1 radius of opening
W width of the ring-shaped bottom portion
R radius of inlay
H height of inlay
A axis of flask
62 folding
64 aligning the crease line parallel to the axis of the flask
66 inserting the folded inlay into the flask
68 unfolding the inlay
70 c-shaped or half-moon-shaped element
72 second opening
74 recess
76 light emitting diode
r oxygen-transfer rate (mmol/(l*h))
t time (hours)

What is claimed is:

1. An inlay for a flask, the inlay comprising:

a bottom portion comprising a downward-facing or downward-and-outward-facing first surface for abutting a bottom inner surface of the flask;

a side portion comprising an outer surface for abutting a side inner surface of the flask, wherein the outer surface faces outwards with respect to a vertical reference line intersecting the inlay wherein said inlay comprises a first elastomer material and said side portion is inwardly bendable and said first elastomer provides an elastic restoration force against inward bending;

an intermediate portion mechanically connecting the bottom portion and the side portion; and a baffle element extending away from the bottom portion, from the side portion, and/or from the intermediate portion for extending into an inner volume of the flask; wherein an inner angle between the first surface and the outer surface is at least 50°, wherein the inner angle refers to an angle on the side of the vertical reference line in a vertical cross section through the inlay; and wherein said bottom portion provides a horizontal crease line and comprises a second elastomer material and said inlay is foldable along said crease line and said second elastomer material provides a restoration force against folding along said crease line.

2. The inlay according to claim 1, wherein a ratio of a height of the inlay along the vertical direction and a maximum width of the inlay in a horizontal direction is at most 0.5.

3. The inlay according to claim 1, wherein the inlay is an integral part.

4. The inlay according to claim 1, wherein the intermediate portion or an outward-facing surface of the intermediate portion extends from the outer surface to the first surface.

5. The inlay according to claim 1 further comprising a flask wherein:

said inlay is engaged to said flask via a force-fit connection of the first surface to the bottom inner surface of the flask and/or a force-fit connection of the outer surface to the side inner surface of the flask.

6. The inlay according to claim 1, wherein the downward-facing or downward-and-outward-facing first surface is a downward-facing bottom surface of the bottom portion.

7. The inlay according to claim 1, wherein, in a horizontal plane intersecting the bottom portion, a shape of the bottom portion is a ring segment or a ring.

8. The inlay according to claim 1, wherein the bottom portion and the first surface comprise an opening.

9. The inlay according to claim 5, wherein the bottom portion comprises or is composed of the first elastomer.

10. The inlay according to claim 1, wherein the first surface extends in a horizontal plane.

11. The inlay according to claim 1, wherein the baffle element extends upwards from the bottom portion.

12. The inlay according to claim 1, wherein the flask is an Erlenmeyer flask.

13. The inlay for the flask according to claim 1, wherein the bottom portion comprises the downward-facing first surface for abutting the bottom inner surface of the flask.

* * * * *